(12) United States Patent
Finjan et al.

(10) Patent No.: US 9,655,835 B2
(45) Date of Patent: May 23, 2017

(54) OIL-CONTROLLING COSMETIC POWDER

(71) Applicant: ELC MANAGEMENT LLC, Melville, NY (US)

(72) Inventors: Talal Finjan, Toronto (CA); Syed Rizvi, Brampton (CA); John R. Castro, Huntington Station, NY (US)

(73) Assignee: ELC Management LLC, Melville, NY (US)

(*) Notice: Subject to any disclaimer, the term of this patent is extended or adjusted under 35 U.S.C. 154(b) by 0 days.

(21) Appl. No.: 14/881,934

(22) Filed: Oct. 13, 2015

(65) Prior Publication Data

US 2016/0101033 A1   Apr. 14, 2016

Related U.S. Application Data

(60) Provisional application No. 62/063,433, filed on Oct. 14, 2014.

(51) Int. Cl.
| | | |
|---|---|---|
| *A61K 8/64* | (2006.01) | |
| *A61Q 1/02* | (2006.01) | |
| *A61Q 1/12* | (2006.01) | |
| *A61K 8/29* | (2006.01) | |
| *A61K 8/25* | (2006.01) | |
| *A61K 8/19* | (2006.01) | |
| *A61K 8/89* | (2006.01) | |
| *A61K 8/02* | (2006.01) | |
| *A61K 8/44* | (2006.01) | |
| *A61Q 19/00* | (2006.01) | |
| *A61K 8/891* | (2006.01) | |

(52) U.S. Cl.
CPC .............. *A61K 8/645* (2013.01); *A61K 8/022* (2013.01); *A61K 8/0241* (2013.01); *A61K 8/0258* (2013.01); *A61K 8/19* (2013.01); *A61K 8/25* (2013.01); *A61K 8/29* (2013.01); *A61K 8/44* (2013.01); *A61K 8/891* (2013.01); *A61Q 1/02* (2013.01); *A61Q 1/12* (2013.01); *A61Q 19/00* (2013.01)

(58) Field of Classification Search
CPC . A61K 8/022; A61K 8/19; A61K 8/25; A61K 8/29; A61K 8/645; A61K 8/891; A61K 2800/43; A61K 2800/432; A61K 2800/596; A61K 8/0241; A61K 8/0258; A61K 8/44; A61K 8/4973; A61K 8/965; A61Q 1/02; A61Q 1/12; A61Q 19/00
See application file for complete search history.

(56) References Cited

U.S. PATENT DOCUMENTS

| | | | |
|---|---|---|---|
| 4,877,604 A * | 10/1989 | Schlossman | A61K 8/25 424/63 |
| 5,683,706 A | 11/1997 | LaFleur et al. | |
| 5,897,868 A * | 4/1999 | Kobayashi | A61K 8/11 424/401 |
| 6,964,773 B1 | 11/2005 | Morrison | |
| 2002/0094341 A1* | 7/2002 | Jorgensen | A61K 8/0295 424/401 |
| 2004/0071747 A1 | 4/2004 | Kume et al. | |
| 2004/0086473 A1 | 5/2004 | Rabe et al. | |
| 2004/0120911 A1* | 6/2004 | Shah | A61K 8/26 424/70.11 |
| 2004/0265347 A1 | 12/2004 | Auguste et al. | |
| 2006/0008441 A1* | 1/2006 | Kanji | A61K 8/891 424/70.121 |
| 2006/0024375 A1* | 2/2006 | Hasegawa | A61K 8/44 424/489 |
| 2007/0254039 A1 | 11/2007 | Witham et al. | |
| 2011/0110992 A1* | 5/2011 | Garrison | A61K 8/25 424/401 |

FOREIGN PATENT DOCUMENTS

WO   WO-2010/111279   9/2010

OTHER PUBLICATIONS

ARCH; Arch Personal Care Products; www.archpersonalcare.com; Cosmetic Ingredients & Ideas; Bio-Pol OE, VegePol, VegaPol W; Biopolymers for sebum control; May 2007. (7 pgs.).
KOBO Products, Inc.; www.koboproducts.com; Hybrid Surface Treatments; USA & Canada Program; Technical Literature ref. Hybrid-002; Sep. 2012. (2 pgs.).
PCT Int'l Search Report; Int'l Application No. PCT/US2015/055342; Completion Date: Jan. 26, 2016; Date of Mailing: Jan. 26, 2016.
PCT Written Opin of the Int'l Searching Authority; Int'l Application No. PCT/US2015/055342; Completion Date: Jan. 26, 2016; Mailing Date: Jan. 26, 2016.

* cited by examiner

*Primary Examiner* — Mark V Stevens
(74) *Attorney, Agent, or Firm* — Cynthia R. Miller

(57) ABSTRACT

A powder-based cosmetic composition for application to skin is provided. The composition contains (a) one or more cosmetically acceptable particulates which are naturally hydrophobic or coated with a hydrophobic material; (b) at least one binder for the particulates of the powder-based cosmetic composition; and (c) a film-forming, oil-absorbing polymer having an affinity for sebum secreted from skin.

18 Claims, No Drawings

OIL-CONTROLLING COSMETIC POWDER

BACKGROUND OF THE INVENTION

Field of the Invention

The present invention relates to powder-based cosmetic compositions having improved performance characteristics. More specifically, the present invention is concerned with powder-based cosmetic compositions having a high affinity for keratinous surfaces which demonstrate improved transfer-resistance, long-wear, good coverage and oil-controlling properties. Moreover, the compositions feel silky and comfortable on the skin.

Description of the Prior Art

Women continually seek cosmetic products for application to skin, such as makeup foundation, pressed powder, blush and eyes shadow, that maintain their fresh look for extended periods of time and which exhibit transfer resistance. Powder-based cosmetics are well known. They are typically provided in solid form and comprise a major portion of powdered material, such as fillers and pigments, together with a binder, if the product is intended to be pressed into a container. Nevertheless, many such products tend to lack substantivity with the skin, and therefore are easily transferred to surfaces and must be reapplied frequently to main a fresh look. A major disadvantage with powder-based cosmetics which purport to provide long wear is that the extended wear is typically achieved by using solvents, waxes and/or polymers which adversely affect the feel of the product on the skin. Moreover, such ingredients can be irritating to skin. A further disadvantage of some known powder-based cosmetics is that they are composed substantially of talc. Talc is used as an absorbent, an opacifier, and to improve the feel of a product. Nevertheless, as an absorbent, talc not only soaks up oil, but, over time, also steals moisture from the product, causing it to lose its luxurious feel. Some products include silicon forming resins which can flake off. To address that problem, silicon-forming resins have been combined with plasticizers, but the resulting film may feel tacky on the skin.

There therefore remains a need for powder-based cosmetics which require fewer applications by consumers and have the attributes of a silky feel, long wear, transfer-resistance, resistance to streaking, longer lasting color and oil absorption, particularly under high humidity conditions.

SUMMARY OF THE INVENTION

The present invention provides long-wearing, oil absorbing and humidity-resistant cosmetic products, in particular, powder-based cosmetic products with high affinity for keratinous surfaces.

A powder-based cosmetic composition for application to skin, said composition comprises:

(a) one or more cosmetically acceptable particulates, the particulates being naturally hydrophobic or being coated with a hydrophobic material;

(b) at least one binder for the particulates of the powder-based cosmetic composition; and (c) a film-forming, oil-absorbing polymer having an affinity for sebum secreted from skin.

DETAILED DESCRIPTION OF THE PREFERRED EMBODIMENTS OF THE INVENTION

Consumers are always in search of make up with staying power; that is, make up that resists smudging and transfer for 8 hours, 12 hours, or even 24 hours. Long wear products have been around for decades. Nevertheless, products like wear like cement on the skin are undesirable. Consumers seek make up that both looks and feels good on their skin, and which requires fewer or no touch ups throughout the day. Such products should also be lightweight with good coverage, and should be comfortable to wear for an extended period of time without caking, drying, or sliding into creases. Long wear products for use on eyes and facial skin are particularly desired by consumers in hot, humid climates.

"Long wear" compositions, as used herein, refers to compositions where the product remains affixed to the keratinous substrate, and color remains substantially the same at the time of the initial application of product, as viewed by a trained expert, after an extended period of time. Long wear properties may be measured by any method known in the art for evaluating such property. For example, long wear may be evaluated by as test involving the application of a composition to the facial skin, and evaluating the color of the composition and whether the composition remains even or becomes streaked after various periods of time. The appearance of the composition may be evaluated immediately upon application to the skin and then re-evaluated and compared to the appearance of the initial application after certain periods of time.

"Transfer-resistance" as used herein refers to the quality exhibited by compositions that are not readily removed by contact with another material, such as, for example, an item of clothing. Transfer-resistance may be evaluated by any method known in the art for evaluating such property. For example, transfer-resistance of a composition may be evaluated by the amount of product transferred from a wearer to any other substrate, such as transfer from the facial skin to an individual's collar when putting on or taking off clothing after the expiration of a certain amount of time following application of the composition to the skin. The amount of composition transferred to the collar may then be evaluated and compared. For example, the compositions may be transfer-resistant if a majority of the product is left on the wearer's skin.

"Oil-controlling" as used herein means a property of a cosmetic that provides a long term matte finish after application to skin without pooling of oil.

"Humidity resistant" as used herein means a property of a cosmetic that is long-wearing, sweat-free, and transfer-proof.

"Particulates" refers to a pulverulent or powder phase, including cosmetically acceptable fillers and colorants, including pigments, and the like, as defined herein, useful in powder-based compositions according to the present invention, such as loose powders, pressed powders, including foundation, blush, eyeshadow, and also cream to powder formulations.

"Hydrophobic" as used herein with regard to surface treatments of particulates means rendering the particulates resistant to attracting or mixing with water.

"Lipophilic" as used herein with regard to surface treatments of particulates means rendering the particulates compatible with natural and synthetic oils, esters, and silicones.

Typically, long wear, humidity resistant and/or oil-control cosmetic products have taken the form of oil-free sheer liquids, creamy foundations and compact powders. Silicones and film-forming resins have long been the mainstay of long wear makeup formulas. Silicone resins, with their film-forming attributes, hold pigments in place and impart water-resistance. Such products containing these silicone resins are typically combined with volatile materials. When the volatile component flashes off, a flexible layer of film remains for long-lasting wear. Advances in polymer technology have imparted improved adherence of long wear products to skin as well as affording softer textures of such formulations. Alternatively, consumers have relied on primer products, applied under conventional foundation or eye makeup products, to achieve the long wear result.

Most pigments and fillers have a naturally hydrophilic surface with polar hydroxyl groups, and therefore tend to absorb water. Such pigments demonstrate agglomeration, poor wettability and dispersibility in cosmetic fluids, poor dispersion stability and poor formulation stability, poor pressibility in pressed powders, and poor chemical stability of metal oxides. Surface treatment can improve the performance of pigment and fillers all the aforementioned aspects so as to make them more compatible in cosmetic formulations.

A variety of surface treatments are known. While methicone can be used to provide a crosslinked coating on pigments, for example, which is hydrophobic and stable over a range of pH of about 3-9, formulations containing these treated pigments tend to leave skin feeling dry. Additionally, the treated pigments are not very compatible with esters and oils. A crosslinked coating of dimethicone provides improved slip compared with methicone but is less hydrophobic. The combination of methicone with a relatively small amount of dimethicone demonstrates improved hydrophobicity compared with the use of either methicone or dimethicone alone.

Pigments coated with organosilicone compounds, such as alkoxysilanes, for example, triethoxycaprylylsilane, demonstrate excellent hydrophobicity, and improved compatibility with esters and oils as compared with methicone and dimethicone. Additionally, such pigments have good compatibility with binders, demonstrate good compressibility properties, and provide a creamy feel.

Pigments treated with amino acid, such as acyl amino acids having, for example, lauroyl, myristoyl, or stereoyl constituents, are weakly acidic and tend to be non-irritating as they have the approximate pH of human skin. These treated pigments are particularly stable in water-in-oil and in water-in-silicone emulsions, and further demonstrate improved processibility and dispersibility. Powder-based cosmetic compositions containing such acid-treated pigments or powders are known. Nevertheless, amino acid-treated pigments or powders are not easily dispersed in lipophilic vehicles.

Further coating amino acid treated pigments or fillers with an alkyl silane, such as triethoxycaprylylsilane, a silicone, for example, dimethicone trimethylsiloxysilicate, or a fatty acid, for example, an organo titanate, such as isopropyl titanium triisostearate (ITT), renders the powders and pigments more lipophilic, making them more easily dispersible with silicones and esters. The additional surface treatment also improves skin adhesion and wear resistance. Such pigments impart moisturizing properties and a smooth feel to the formulations into which they are incorporated. The organo titanates may also be used alone as a coating on pigments to render pigments lipophilic, with a high affinity for skin because of the presence of the fatty group. The organo titanates also impart improved compressibility to pressed powders. However, the hydrophobicity of such coated pigments is less than that of pigments coated with silicones. A preferred surface treatment of this type is isopropyl titanium triisostearate & sodium lauroyl aspartate & zinc chloride (ASI). ASI-treated-iron oxides, -mica, —TiO$_2$, -sericite, and -talc, available from Kobo, are particularly suited for use in pressed powders and in emulsions.

A further surface treatment for pigments or fillers is a crosspolymer treatment, such as, crosspolymers comprised of ITT in combination with alkoxysilane, methicone or dimethicone. Such crosspolymers render the pigments both hydrophobic and lipophilic, and superdispersible in esters/hydrocarbons and silicones. Examples of the crosspolymers include ITT/triethoxycaprylylsilane crosspolymer, ITT/methicone crosspolymer and ITT/triethoxysilylethyl polydimethylsiloxyethyl dimethicone crosspolymer.

Particulates, including metal oxides, such as titanium dioxide, iron oxides, zinc oxide, and aluminum oxide, even when coated with a silicone or a silane, demonstrate poor dispersibility in esters, vegetable oils, mineral oil and hydrocarbons. Poor dispersibility can adversely affect color strength in pigments, as well as skin feel and formulation stability. It is known to surface treat particulate metal oxides with organic dispersants, such as the polyester, polyhydroxystearic acid, to render the particles self-dispersible. Prior to treatment with the organic dispersant, a first, inorganic coating may be applied to the particles. The inorganic materials may include oxides of other elements, such as aluminum, zirconium or silicon. A further optional hydrophobic coating may be applied over the inorganic coating. Hydrophobic coatings may consist of, for example, silicones, such as methicone or dimethicone, copolyols thereof, or organosilicones; silanes, such as alkoxysilane, for example, alkyltriethoxy or alkyltrimethoxy silanes, such as triethoxycapryl silane; metal soap, such as a metal myristate, a metal stearate, a metal palmitate or a metal laurate; or a fatty acid, such as lauric acid, stearic acid, isostearic acid, and salts of those fatty acids, for example, isopropyl titanium triisostearate (ITT). One example of this type of treated particle is 11SP, available from Kobo. The treated particles may be used in cosmetic liquid make ups and dry formulations, such as foundation, pressed powder, blush, eyeshadow, and so forth. Such treated particles may be used in pressed powders using dimethicone as the sole liquid binder, while providing a creamy feel with excellent spreadability.

While the use of hydrophobically- or lipophilically-treated pigments and fillers, such as treated pigments and fillers of the type discussed hereinabove, formulated into cosmetic products, is said to demonstrate a measure of long wear, transfer-resistance, humidity resistance and oil control, the inventors have discovered, surprisingly and unexpectedly, that powder-based cosmetic compositions containing such treated particulates, and at least one binder for the particulates of the powder-based composition, when further combined with a film-forming, oil-absorbing polymer material, demonstrate exceptionally improved wear, superior sweat- and humidity-resistance and oil control. The film-forming, oil-absorbing material facilitates even spreading of sebum exuded from the skin, thus preventing pooling of sebum and oil breakthrough which could result in discoloration of the makeup on the skin (due to areas which darken due absorption of or pooling of oil) and reduced wear and transfer-resistance.

Powder-based compositions of the invention are composed of (a) one or more cosmetically acceptable particulates, said cosmetically acceptable particulates being naturally hydrophobic or coated with a hydrophobic material; (b) at least one binder for the particulates of the powder-based cosmetic composition; and (c) an oil-absorbing polymer having an affinity for sebum secreted from skin. Powder-based compositions of the present invention may take the form of, for example, an anhydrous or substantially anhydrous powder, such as a pressed powder, or a liquid-to-powder or cream-to-powder formulation.

The particulates useful in the compositions of the present invention include pigments and fillers which are naturally hydrophobic or surface treated to render them hydrophobic.

The naturally hydrophobic or surface treated pigments and/or fillers may be used in the powder-based compositions according to the invention in amounts in the range of from about 25% to about 99%, preferably from about 65% to about 95%, more preferably, from about 75% to about 85%, by weight of the total composition. Particulates useful in the compositions of the invention have an average particle size in the range of from about 0.01 to about 100 microns.

The term "fillers" should be understood as meaning colorless or white, mineral or synthetic particles of any shape, which are insoluble in the medium of the composition, irrespective of the temperature at which the composition is manufactured. Fillers include, but are not limited to, silica microspheres, including hollow silica microspheres, and acrylic polymer microspheres, such as those made of crosslinked acrylate copolymer, and those made of polymethyl methacrylate; polyurethane powder such as the powder of a copolymer of hexamethylene diisocyante and of trimethylol hexyl lactone; elastomeric crosslinked organopolysiloxane spherical powders; carnauba or paraffin wax microbeads; metal soaps in powder form, including metal soaps of fatty acids containing from 12 to 22 carbons, where the metal of the metal soap may be zinc or magnesium, and the fatty acid may be chosen especially from lauric acid, myristic acid, stearic acid and palamitic acid, for example, zinc laurate, magnesium stearate, magnesium myristate and zinc stearate, and mixtures thereof; talcs or hydrated magnesium silicates; micas or aluminosilicates, the micas possibly being of natural origin (for example muscovite, margarite, roscoelite, lipidolite or biotite) or of synthetic origin; clays such as sericites, which belong to the same chemical and crystalline class as muscovite; kaolin or hydrated aluminum silicate; boron nitrides; powders of tetrafluoroethylene polymers; precipitated calcium carbonate; magnesium carbonate and magnesium hydrogen carbonate; hydroxyapatite; powders of non-expanded synthetic polymers, such as polyethylene, polyesters (for example polyethylene isophthalate or terephthalate) and polyamides (for example Nylon; powders of spheronized, crosslinked or non-crosslinked synthetic polymers, for instance polyamide powders such as poly-P-alanine powder or Nylon powder, such as polyacrylic acid or polymethacrylic acid powder, powders of polystyrene crosslinked with divinylbenzene, and silicone resin powders; bismuth oxychloride powders; powders of organic materials of natural origin, for instance starches, especially corn starch, wheat starch or rice starch; and mixtures thereof. As representatives of such fillers, mention may especially be made of titanium oxides, zinc oxides, iron oxides and bismuth oxychloride powders.

A composition according to the invention may also comprise, in its pulverulent phase, a coloring agent. The coloring agent or dyestuff according to the invention is chosen from pigments, nacres and reflective particles, and mixtures thereof.

The term "pigments" should be understood as meaning white or colored, mineral or organic particles of any form, which are insoluble in the physiological medium and are intended to color the composition. Among the mineral pigments that may be mentioned are titanium dioxide, zirconium oxide or cerium oxide, and also zinc oxide, iron (black, yellow or red) oxide or chromium oxide, sericites, micas, talcs, kaolin, manganese violet, ultramarine blue, chromium hydrate and ferric blue, and metal powders, such as aluminum powder and copper powder. Naturally hydrophobic minerals, include talc, starch, and the like. The organic pigments may include cochineal carmine, carotenoids, curcumin, porphyrin pigment, and vegetable carbon black; organic pigments of azo dyes, anthraquinone dyes, indigoid dyes, xanthene dyes, pyrene dyes, quinoline dyes, triphenylmethane dyes and fluorane dyes. Synthetic pigments include ultramarines.

Among the organic pigments, mention may be made of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

According to another embodiment, a composition according to the invention may be free of pigments.

The pulverulent phase according to the invention may also comprise, or may even be formed from, nacres and/or reflective particles. The term "nacre" should be understood as meaning colored particles of any form, which may or may not be iridescent, especially produced by certain molluses in their shell, or alternatively synthesized, and which have a color effect via optical interference. Examples of nacres that may be mentioned include nacreous pigments such as titanium mica coated with an iron oxide, mica coated with bismuth oxychloride, titanium mica coated with chromium oxide, and also nacreous pigments based on bismuth oxychloride. They may also be mica particles at the surface of which are superposed at least two successive layers of metal oxides and/or of organic dyestuffs. Still as examples of nacres, mention may also be made of particles comprising a borosilicate substrate coated with titanium oxide.

The term "reflective particles" denotes particles whose size, structure, especially the thickness of the layer(s) of which they are made and their physical and chemical nature, and surface state allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle. The reflective particles may be selected so as not to significantly alter the coloration effect generated by the coloring agents with which they are combined, and more particularly so as to optimize this effect in terms of color yield. They may more particularly have a yellow, pink, red, bronze, orange, brown, gold and/or coppery color or tint. These particles may have varied forms and may especially be in platelet or globular form, in particular spherical. Irrespective of their form, the reflective particles may or may not have a multilayer structure, and, in the case of a multilayer structure, for example at least one layer of uniform thickness, especially a reflective material. When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be a monomaterial, multimaterial, organic and/or mineral substrate. More particularly, it may be chosen from glasses, ceramics, graphite, metal oxides, aluminas, silicas, silicates, especially aluminosilicates and borosilicates, and synthetic mica, and mixtures thereof. The reflective material may comprise a layer of metal or of a metallic material.

Particles comprising a metallic substrate such as silver, aluminum, iron, chromium, nickel, molybdenum, gold, copper, zinc, tin, manganese, steel, bronze or titanium, may also be used, said substrate being coated with at least one layer of at least one metal oxide such as titanium oxide, aluminum oxide, iron oxide, cerium oxide, chromium oxide or silicon oxides, and mixtures thereof. Also useful in the compositions of the present invention are particles having a glass substrate, such as soda lime glass beads, beady beads (aluminum calcium sodium silicate), or glass coated with titanium oxide polyethylene terephthalate flakes.

Materials useful for treating the particulates of the compositions of the present invention, so as to render these hydrophobic and/or lipophilic, may be selected from, as examples, amino acids, fatty acids, silicones, silanes, metal soaps and waxes.

Amino acids may be acyl amino acids, including, lauroyl, myristoyl and steareoyl amino acids, for example sodium lauroyl aspartate.

Fatty acids may be those containing 10-20 carbon atoms, such as lauric acid, stearic acid, isostearic acid, and salts thereof. For example, the fatty acid may be organo titanate, such as isopropyl titanium triisostearate. Silicones may be selected from methicone, dimethicone, a copolymer of methicone and dimethicone, and an organosilicone compounds. The organosilicone compounds may preferably be selected from a dimethylpolysiloxane having a backbone of repeating -Me$_2$SiO— units, a methyl hydrogen polysiloxane having a backbone of repeating -MeHSiO— units, and an alkoxysilane of formula R$_n$OSiH$_{(4-n)}$ where R is alkyl and n is the integer 1, 2 or 3, and mixtures thereof.

The silane may be an alkoxysilane selected from alkyltriethoxy and alkytrimethoxy silanes. For example, the alkoxysilane may be a triethoxycaprylylsilane or a perfluoroalkylethyl triethoxysilane having a C$_3$ or C$_{12}$ alkyl group that is straight or branched.

The metal soap may be chosen from among metal myristates, metal stearates, metal palmitates, metal laurates, and mixtures thereof. The metal may be magnesium, zinc or aluminum. Among these soaps, mention may be made of metal soaps of fatty acids containing from 12 to 22 carbon atoms and in particular those containing from 12 to 18 carbon atoms. The metal of the metal soap may especially be zinc or magnesium. The fatty acid may be chosen especially from lauric acid, myristic acid, stearic acid and palmitic acid. Examples of metal soaps that may be used include zinc laurate, magnesium stearate, magnesium myristate and zinc stearate, and mixtures thereof.

Organic waxes may be synthetic wax or natural wax. As examples, polyethylene or carnauba wax may be used.

In a preferred embodiment of the invention, the particulates in the powder compositions of the present invention comprise particles and/or flakes of mica and/or iron oxides which are surface treated with isopropyl titanium triisostearate, sodium lauroyl aspartate and zinc chloride.

Preferred cosmetic powder binders useful in the compositions of the present invention, are silicone resins, including silanes, siloxanes, siloxysilicates and silsesquioxanes. Silicone resin nomenclature is referred to in terms of "MDTQ" nomenclature, whereby a silicone resin is described according to the various monomeric siloxane units which make up the polymer. Each letter of "MDTQ" denotes a different type of unit. The letter M denotes the monofunctional unit (CH$_3$)$_3$SiO$_{1/2}$. This unit is considered to be monofunctional because the silicone atom only shares one oxygen when the unit is part of a polymer. The symbol D denotes the difunctional unit (CH$_3$)$_2$SiO$_{2/2}$ wherein two oxygen atoms bonded to the silicone atom are used for binding to the rest of the polymer. The symbol T denotes the trifunctional unit (CH$_3$)SiO$_{3/2}$ wherein three oxygen atoms bonded to the silicone atom are used for binding to the rest of the polymer. The symbol Q denotes the tetrafunctional unit SiO$_{4/2}$ wherein all four oxygens bonded to the silicone atom are bonded to the rest of the polymer.

A non-limiting example of a siloxane useful in the compositions of the present invention is a polydimethylsiloxane (PDMS). Polydimethylsiloxanes are generally composed of long straight chains of (CH$_3$)$_2$SiO$_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the formula:

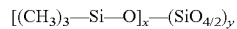

$$[(CH_3)_3-Si-O]_x-(SiO_{4/2})_y$$

(i.e, MQ units) wherein x and y may, for example, range from 50 to 80.

Silsesquioxanes may be represented by the formula: (CH$_3$SiO$_{3/2}$)$_x$ (i.e., T Units) wherein x may, for example, have a value of up to several thousand, for example up to one thousand, such as from about 50 to about 500 units. Polymethylsilsesquioxane, available as Tospearl, has both M and T units.

In one preferred embodiment of the invention, the cosmetic powder binder comprises at least one silicone resin having M and Q units, such as a siloxysilicate, for example, trimethylsiloxysilicate. In another preferred embodiment of the present invention, the cosmetic powder binder comprises at least one silicone resin having M and Q units, such as trimethylsiloxysilicate, and at least one further silicone resin having M and T units, for example, a silsesquioxane, such as polymethylsilsesquioxane.

Compositions of the present invention may include one or more additional binders. Preferred additional binders include, for example, dimethicone (polydimethylsiloxane fluid), dimethicone silylate/isododecane, and polyglyceryyl-2 triisostearate, and dry binders such as zinc, lithium and magnesium stearate.

Binders may be present in the compositions of the invention in amounts in the range of from about 0.1%-20% by total weight of the powder-based cosmetic composition.

Film-forming, oil-absorbing polymer materials useful in the compositions of the invention are those having polar and non-polar regions, and which upon contact with the sebum secreted from the skin, break up the sebum into individual droplets and entrap the individual droplets in the film.

In a preferred embodiment of the present invention, the polymers are heteropolymers having a protein backbone with lipophilic sidechain groups. The heteropolymers have a strong attraction to oil, but cannot penetrate into the oil because of the protein backbone. The heteropolymers attach to the oil, break the oil up into droplets, and entrap the droplets into a film, thus isolating the oil droplets from the powder-based cosmetic composition and preventing pooling of oil and oil breakthrough to the surface of the powder composition. Such heteropolymers have been used in liquid foundations to normalize sebum deposition as an alternative to the using of powder foundations to control the flow of skin lipids. Preferably, the heteropolymers are composed of between 100 and 300 repeating units or residues with total a molecular weight of between 10 kDa and 30 kDa. Examples of such heteropolymers may include $C_2$-$C_{16}$ acetylated lactoglobulin, for example, sodium $C_8$-$C_{16}$ isoalkylsuccinyl lactoglobulin sulfonate, available as Bio-Pol® OE, from Arch Personal Care Products, or a vegetable-based derivative thereof, such as sodium $C_8$-$C_{16}$ isoalkylsuccinyl soy protein sulfonate or sodium $C_8$-$C_{16}$ isoalkylsuccinyl wheat protein sulfonate, available as Veg-ePol or VegePol W, respectively, both available from Arch Personal Care Products. Heteropolymers comprising sterols, such as cholesterol or fatty acids, such as linoleic acid, may also be useful in the compositions of the invention. The film-forming, oil-absorbing material will be present in the compositions of the present invention in amounts in the range of from about 0.1% to about 10%, and preferably from about 0.5% to about 5%, such as from about 1% to about 3% by total weight of the composition.

In a particularly preferred embodiment of the present invention, the powder-based composition comprises mica coated with isopropyl titanium triisostearate; sodium lauroyl aspartate and zinc chloride, iron oxides coated with isopropyl titanium triisostearate, sodium lauroyl aspartate and zinc chloride; trimethylsiloxysilicate; polymethylsilsesquioxane; dimethicone; dimethicone silylate/isododecane; polyglyceryl-2 triisostearate; zinc stearate; and a polymer comprising hydrolyzed soy protein and coconut acid.

In preferred embodiments of the invention, the compositions are anhydrous or substantially free of water. By "substantially free of water" it is intended that the compositions contain less than 5%, preferably less than 3%, and most preferably the compositions contain 0% water, based on the total weight of the composition.

The invention may take the form of loose or pressed powders, but may also be in the form of a liquid or cream formulation which dries down quickly to powder after application to skin. Such liquid-to-powder or cream-to-powder formulations will contain one or more volatile solvents but substantially no water. Volatile solvents include any non-aqueous medium capable of evaporating on contact with the skin in less than one hour at room temperature and atmospheric pressure. Examples of suitable volatile solvents may include hydrocarbon-based oils and linear or cyclic silicone oils. The volatile solvents may be present in the formulations in amounts in the range of from about 15 to about 75 weight percent, based on the total weight of the formulation. The formulation may also contain water-soluble actives, botanicals and preservatives.

Incorporating the film-forming, oil-absorbing polymer, a surfactant-like material, into anhydrous or substantially anhydrous pressed powder compositions or into liquid-to-powder or cream-to-powder formulations of the present invention is counterintuitive, since, as the formulations contain little or no water, so there is no need for a surfactant to stabilize the formulation by compatibilizing water and oil phases. In compositions of the present invention, the film-forming, oil-absorbing polymer, although having a structure similar to that of a surfactant, does not act like a surfactant. Surprisingly and unexpectedly, this material breaks sebum secreted from the skin in to droplets and coats those droplets with a film in a micelle-like manner on the skin surface. Pooling of oil on the skin, which tends to discolor the powder cosmetic, and slipping off of the powder cosmetic composition from the skin are avoided even in hot and/or humid environments.

Additional ingredients may be incorporated in the cosmetic powders to improve texture, pressability and finish. In particular, the compositions may include powdered lubricants which help in forming the composition as well as improving the application and adherence of the composition to skin. Such lubricants contribute a smooth, silky feel to the powder, and may include, but are not limited to, boron nitride, metal stearates (e.g. zinc, aluminum, magnesium, potassium, calcium, lithium and combinations thereof), T resins, including polymethylsilequioxane, such as Tospearl, and spherical silica. If used, the lubricants are present in the compositions in amounts in the range of from about 0.1 to about 10 percent by total weight of the compositions.

Powdered absorbers or sorbent agents aid in absorption of excess oil on skin, help maintain color trueness of the cosmetic product, and also facilitate binding of the ingredients and aid in the pressibility of the powder without adversely affecting pay-off from a pressed tablet. Such sorbent agents may include, but are not limited to, silicates (e.g., aluminum, calcium, sodium or combinations thereof) and silicone resin microbeads, including polymethylsilequioxane, such as sold under the name Tospearl which, if present, also contribute to a reduction in agglomeration in pressed powders, and provide a soft focus effect, which minimizes the appearance of lines and wrinkles in the skin. Sorbent agents are preferably present in an amount of from about 0.5 to 20% by total weight of the composition.

Compressed products may be made by mixing or blending powders until uniform, adding solvents, including oils, compressing the mixture into a suitable container using conventional tablet pressing equipment and techniques commonly used in the cosmetic and/or pharmaceutical industries. Esters and emollient oils which may be added to modify the powder, include, but are not limited to, silicone oils, natural plant oils like soybean, polyglyceryl esters, and squalane.

The invention will be illustrated by, but is not intended to be limited to, the following examples.

EXAMPLES

Example 1—Pressed Powder

| Sequence | Materials | Weight percent |
|---|---|---|
| 1 | mica/isopropyl titanium triisostearate/sodium lauroyl aspartate/zinc chloride | 39.9199 |
| 1 | zinc stearate | 4.0000 |
| 1 | titanium dioxide/triethoxycaprylsilane | 9.0000 |
| 1 | cholesterol | 0.1000 |
|   | ascorbyl palmitate | 0.1000 |
| 1 | iron oxides/isopropyl titanium triisostearate/zinc chloride/sodium lauroyl aspartate | 1.2100 |
| 1 | ultramarine blue | 0.0001 |
| 1 | trimethylsiloxysilicate | 2.0000 |
| 2 | boron nitride/methicone | 5.0000 |
| 2 | polymethylsilsesquioxane | 5.0000 |
| 2 | silica | 5.0000 |
| 2 | HDI/trimethylol hexyllactone cross-polymer//silica | 5.0000 |
| 2 | aluminum calcium sodium silicate | 4.0000 |
| 2 | soda lime glass beads | 5.0000 |
| 3 | caprylyl glycol/phenoxyethanol/hexylene glycol | 0.5000 |
| 4 | water/hydrolyzed soy protein/coconut acid | 1.0000 |

-continued

| Sequence | Materials | Weight percent |
|---|---|---|
| 4 | dimethicone | 1.8400 |
| 4 | dimethicone silylate/isododecane | 3.6800 |
| 4 | polyglyceryl-2 triisostearate | 2.4500 |
| 4 | squalane/*Hordeum vulgare* (barley) extract *triticum vulgare* (wheat) extract | 0.1000 |
| 4 | linoleic acid | 0.0500 |
| 4 | soybean extract/ceramide III | 0.0500 |
| 5 | boron nitride/methicone | 5.0000 |
|   | TOTAL | 100.0000 |

Procedure:
1. Sequence 1 ingredients were weighed out and mixed in a blender at 7000 rpm for 1.5 minutes.
2. Sequence 2 and 3 ingredients were added to the blender and the batch mixed at 7000 rpm for 1.5 minutes.
3. Sequence 4 ingredients were added to the blender in three portions with mixing at 7000 rpm for 1.5 minutes after each addition.
4. The batch was scraped and then mixed at 7000 for 1.5 minutes.
5. The batch was pulverized with a 0.2 screen.
6. The batch was ultrarotored.
7. The batch was placed back in the blender, Sequence 5 ingredients were added, and the batch mixed at 7000 rpm for 1.5 minutes.
8. One piece was pressed and color matched to standard.

Example 2—Pressed Powder

| Sequence | Materials | Weight percent |
|---|---|---|
| 1 | mica/isopropyl titanium triisostearate/sodium lauroyl aspartate/zinc chloride | 38.760 |
| 1 | boron nitride/methicone | 10.000 |
| 1 | polymethylsilsesquioxane | 5.000 |
| 1 | silica | 5.000 |
| 1 | zinc stearate | 7.000 |
| 1 | titanium dioxide/triethoxycaprylylsilane | 0.100 |
| 1 | HDI/trimethylol hexyllactone crosspolymer//silica | 5.000 |
| 1 | aluminum calcium sodium silicate | 4.000 |
| 1 | soda lime glass beads | 5.000 |
| 1 | iron oxides/isopropyl titanium triisostrearate/zinc chloride/sodium lauroyl aspartate | 9.240 |
| 1 | cholesterol | 0.100 |
| 1 | ascorbyl palmitate | 0.100 |
| 2 | caprylyl glycol/phenoxyethanol/hexylene glycol | 0.500 |
| 3 | water/hydrolyzed soy protein/coconut acid | 1.000 |
| 4 | dimethicone | 2.700 |
| 4 | dimethicone silylate/isododecane | 2.700 |
| 4 | polyglyceryl-2 triisostearate | 1.800 |
| 4 | trimethylsiloxysilicate | 1.800 |
| 4 | squalane/*Hordeum vulgare* (barley) extract *triticum vulgare* (wheat) extract | 0.100 |
| 4 | linoleic acid | 0.050 |
| 4 | soybean extract/ceramide III | 0.050 |
|   | TOTAL | 100.0000 |

Procedure:
1. Sequence 1 ingredients were weighed out and mixed in a blender at 7000 rpm for 1.5 minutes.
2. Sequence 2 and 3 ingredients were added to the blender and the batch mixed at 7000 rpm for 1.5 minutes.
3. Sequence 4 ingredients were added to the blender in three portions with mixing at 7000 rpm for 1.5 minutes after each addition.
4. The batch was scraped and then mixed at 7000 rpm for 1.5 minutes.
5. The batch was pulverized with a 0.2 screen.
6. One piece was pressed and color matched to standard.

Example 3—Clinical Study

Adult women were recruited from a local population. The following criteria for inclusion and exclusion were based on the information obtained from the candidates and from an examination of the area that was involved in the study.

Inclusion Criteria:
To have been considered as a potential subject, each candidate must have:
normal, fair skin;
been in good general health;
expressed willingness to cooperate with the investigator;
convinced the investigator that she was dependable and would comply with the study regimen;
demonstrated the ability to understand the purpose of the study and what was required of her to bring it to a meaningful conclusion;
demonstrated the ability to understand the risks associated with her participation;
demonstrated the ability to read and understand all the items in the informed consent document;
signed the informed consent document of her own free will and without any reservations.

Exclusion Criteria:
A prospective participant was excluded if the interview or examination disclosed any of the following:
a systemic illness that contra-indicates participation;
any dermatological disorders in the test areas;
that she was under a dermatologists care for any conditions in the test areas;
pregnancy or lactation;
use of Retin-A, Retinol, or AHAs in the past 12 months;
cosmetic procedures in the past 12 months (injectable anti-wrinkle products, facial cosmetic surgery, etc.)
that she is an Estee Lauder Companies employee.

Method of Application:
Participants selected for the panel satisfied all the requirements itemized in the list of inclusion and exclusion criteria. The women were instructed to wear no moisturizer or makeup on the day of testing. The product of Example 2 was applied to the panelists' face by a trained Cosmetologist. Results are summarized in Table 1.

TABLE 1

|  | Color Retention | Streaking | Color Change |
|---|---|---|---|
| Immediate | 100% | Minimal | — |
| 2 hours | 98% | Minimal | None |
| 4 hours | 95% | Minimal | Minimal |
| 6 hours | 90% | Minimal | Mild |
| 8 hours | 87% | Minimal | Mild |
| 10 hours | 83% | Minimal | Mild-moderate |
| 12 hours | 80% | Minimal | Mild-moderate |

Results:
After 12 hours of wear, it was observed that the invention powder:
retained an average of 80% of color
demonstrated minimal creasing
demonstrated mild-moderate color shift It will be apparent to those skilled in the art that various modifications and variations can be made in the compositions of the invention without departing from the spirit or scope of the invention. Thus, it is intended that the present description cover the modifications and variations of this invention provide that they come within the scope of the appended claims and their equivalents.

What is claimed is:

1. A cosmetic powder composition for application to skin, said composition comprising:
   (a) one or more cosmetically acceptable particulates, said cosmetically acceptable particulates being coated with a hydrophobic material, the hydrophobic material comprising at least one fatty acid, at least one acyl amino acid, and zinc chloride, and the particulates being present in an amount in the range of from about 65 to about 95 percent by weight of the total composition;
   (b) at least one binder for the particulates, the binder comprising at least one silicone resin selected from the group consisting of silanes, siloxanes, siloxysilicates and silsesquioxanes, and the binder being present in the range of from about 0.1 to about 20 percent by weight of the total composition; and
   (c) an oil-attracting heteropolymer having a protein backbone with lipophilic sidechains, said heteropolymer being present in a range of from about 0.5 to about 5 percent by weight of the total composition, wherein said heteropolymer breaks up sebum on skin into individual droplets and entraps the individual droplets in a film; and
wherein said powder composition is anhydrous or substantially free of water.

2. The cosmetic powder composition of claim 1, wherein the heteropolymer is a $C_2$-$C_{16}$ acetylated lactoglobulin or a $C_2$-$C_{16}$ acetylated vegetable protein.

3. The cosmetic powder composition of claim 2, wherein the $C_2$-$C_{16}$ acetylated lactoglobulin comprises sodium $C_8$-$C_{16}$ isoalkylsuccinyl lactoglobulin sulfonate.

4. The cosmetic powder composition of claim 2, wherein the $C_2$-$C_{16}$ acetylated vegetable protein is selected from the group consisting of sodium $C_8$-$C_{16}$ isoalkylsuccinyl soy protein sulfonate, sodium $C_{8-16}$ isoalkylsuccinyl wheat protein sulfonate, and combinations thereof.

5. The cosmetic powder composition of claim 1, wherein the particulates are selected from the group consisting of organic pigments, inorganic pigments, fillers, and mixtures thereof.

6. The cosmetic powder composition of claim 5, wherein the inorganic pigments are selected from the group consisting of titanium dioxide, zirconium oxide, cerium oxide, zinc oxide, iron oxides, chromium oxides, sericites, micas, talcs, kaolin, manganese violet, ultramarine blue, chromium hydrate, ferric blue, metal powders, and mixtures thereof.

7. The cosmetic powder composition of claim 5, wherein the organic pigment is selected from the group consisting of cochineal carmine, carotenoids, curcumin, porphyrin pigment, and vegetable carbon black; organic pigments of azo dyes, anthraquinone dyes, indigoid dyes, xanthene dyes, pyrene dyes, quinoline dyes, triphenylmethane dyes, and fluorane dyes, D&C certified colorants, and mixtures thereof.

8. The cosmetic powder composition of claim 1, wherein the acyl amino acid is selected from the group consisting of lauroyl, myristoyl and steareoyl amino acids, and mixtures thereof.

9. The cosmetic powder composition of claim 1, wherein the hydrophobic coating comprises sodium lauroyl aspartate.

10. The cosmetic powder composition of claim 1, wherein the fatty acid contains 10-20 carbon atoms and is selected from the group consisting of lauric acid, stearic acid, isostearic acid, and salts thereof.

11. The cosmetic powder composition of claim 10, wherein the fatty acid comprises isopropyl titanium triisostearate.

12. The cosmetic powder composition of claim 1, comprising particulates coated with isopropyl titanium triisostearate, sodium lauroyl aspartate and zinc chloride.

13. The cosmetic powder composition of claim 1, wherein the binder for the particulates comprises a siloxysilicate.

14. The cosmetic powder composition of claim 13, wherein the siloxysilicate is trimethylsiloxysilicate.

15. The cosmetic powder composition of claim 13, wherein the binder for the particulates further comprises a silsesquioxane.

16. The cosmetic powder composition of claim 15 wherein the silsesquioxane is a polymethylsilsesquioxane.

17. The cosmetic powder composition of claim 15, which comprises at least one further binder for the particulates, said at least one further binder selected from the group consisting of dimethicone (polydimethylsiloxane fluid), dimethicone silylate/isododecane, polyglyceryyl-2 triisostearate, and zinc, lithium and magnesium stearates, and combinations thereof.

18. An anhydrous pressed powder comprising mica coated with isopropyl titanium triisostearate; sodium lauroyl aspartate and zinc chloride; iron oxides coated with isopropyl titanium triisostearate, sodium lauroyl aspartate and zinc chloride; trimethylsiloxysilicate; polymethylsilsesquioxane; dimethicone; dimethicone silylate/isododecane; polyglyceryl-2 triisostearate; zinc stearate; and a heteropolymer selected from the group consisting of a $C_2$-$C_{16}$ acetylated lactoglobulin comprising sodium $C_8$-$C_{16}$ isoalkylsuccinyl lactoglobulin sulfonate; and a $C_2$-$C_{16}$ acetylated vegetable protein selected from the group consisting of sodium $C_8$-$C_{16}$ isoalkylsuccinyl soy protein sulfonate, sodium $C_{8-16}$ isoalkylsuccinyl wheat protein sulfonate; and combinations thereof.

* * * * *